United States Patent
Kaula et al.

(10) Patent No.: US 10,967,186 B2
(45) Date of Patent: Apr. 6, 2021

(54) SYSTEM AND METHOD OF DEVELOPING A PROGRAM FOR PROVIDING THERAPEUTIC ELECTRICAL STIMULATION FOR TREATING A PATIENT

(71) Applicant: CIRTEC MEDICAL CORPORATION, Brooklyn Park, MN (US)

(72) Inventors: Norbert Kaula, Arvada, CO (US); Paul Landers, Lafayette, CO (US); Yohannes Iyassu, Denver, CO (US)

(73) Assignee: CIRTEC MEDICAL CORPORATION, Brooklyn Park, MN (US)

( * ) Notice: Subject to any disclaimer, the term of this patent is extended or adjusted under 35 U.S.C. 154(b) by 0 days.

(21) Appl. No.: 15/952,729

(22) Filed: Apr. 13, 2018

(65) Prior Publication Data
US 2018/0229042 A1 Aug. 16, 2018

Related U.S. Application Data

(62) Division of application No. 14/229,458, filed on Mar. 28, 2014, now Pat. No. 9,943,691.

(51) Int. Cl.
*A61N 1/36* (2006.01)
*A61N 1/372* (2006.01)
*A61N 1/05* (2006.01)

(52) U.S. Cl.
CPC ..... *A61N 1/36185* (2013.01); *A61N 1/36071* (2013.01); *A61N 1/37247* (2013.01); *A61N 1/0553* (2013.01); *A61N 1/36132* (2013.01)

(58) Field of Classification Search
CPC .............. A61N 1/36071; A61N 1/36082
See application file for complete search history.

(56) References Cited

U.S. PATENT DOCUMENTS

| 6,052,624 | A | 4/2000 | Mann |
| 2012/0116476 | A1* | 5/2012 | Kothandaraman ........... A61N 1/36071 607/45 |
| 2012/0310299 | A1 | 12/2012 | Kaula et al. |
| 2012/0310300 | A1 | 12/2012 | Kaula et al. |
| 2012/0310305 | A1 | 12/2012 | Kaula et al. |

* cited by examiner

*Primary Examiner* — Michael J D Abreu
(74) *Attorney, Agent, or Firm* — Haynes and Boone, LLP; J. Andrew Lowes; Eric Q. Li

(57) ABSTRACT

An electronic programmer is used to program a pulse generator to generate electrical stimulation to be delivered to a patient via an implantable lead. The electronic programmer simultaneously displays, via an user interface, a first control mechanism and a second control mechanism that is separate and different from the first control mechanism. A first user input is received via the first control mechanism, and a second user input is received via the second control mechanism. In response to the received first user input and the second user input, the electronic programmer sends instructions to the pulse generator to cause a migration of the electrical stimulation from a first set of electrodes on the implantable lead to a second set of electrodes on the implantable lead. The first user input defines a stimulation amplitude change for the migration, and the second user input defines a direction for the migration.

20 Claims, 13 Drawing Sheets

SYSTEM AND METHOD OF DEVELOPING A PROGRAM FOR PROVIDING THERAPEUTIC ELECTRICAL STIMULATION FOR TREATING A PATIENT

CROSS-REFERENCE TO RELATED APPLICATIONS

This application is a divisional of U.S. Utility application Ser. No. 14/229,458, filed on Mar. 28, 2014, and issued as U.S. Pat. No. 9,943,691 on Apr. 17, 2018, the disclosure of which is incorporated by reference herein in its entirety as if fully set forth below and for all applicable purposes.

BACKGROUND

The invention relates to a stimulation system, such as a spinal cord stimulation (SCS) system, having a tool for programming an electrical stimulation generator, such as an implantable pulse generator (IPG), of the system. The invention also relates to a method for developing a program for the stimulation system.

A spinal cord stimulator is a device used to provide electrical stimulation to the spinal cord for managing pain. The stimulator includes an implanted or external pulse generator and an implanted medical electrical lead having one or more electrodes at a distal location thereof. The pulse generator provides the stimulation through the electrodes via a body portion and connector of the lead. Spinal cord stimulation programming is defined as the discovery of the stimulation electrodes and parameters that provide the best possible pain relief (or paresthesia) for the patient using one or more implanted leads and its attached IPG. The programming is typically achieved by selecting individual electrodes and adjusting the stimulation parameters, such as the shape of the stimulation waveform, amplitude of current in mA (or amplitude of voltage in V), pulse width in microseconds, frequency in Hz, and anodic or cathodic stimulation.

SUMMARY

Numerous embodiments of the invention provide a method and system for programming an electrical stimulator such as a spinal cord stimulator. In SCS systems, paresthesia is achieved by selecting a set of electrodes to target a region in the spinal cord for treating the desired pain area. Generally, a clinician programmer is used to construct a therapeutic program and configure the IPG using a communication media such as Medical Implantable Communication System (MICS). A health care professional (HCP) may begin to construct the therapeutic program by first selecting a target set of electrodes. In addition to selecting the targeted set of electrodes, the HCP can make adjustments to the target set of electrodes by migrating the configured electrode parameters from the initial set of electrodes to a neighboring set of electrodes. Such a system allows the HCP and patient achieve a successful programming session.

In one embodiment, the invention provides a method of developing a program for providing therapeutic electrical stimulation for treating a patient with a stimulation system. The stimulation system comprises an electrical stimulation generator and an implanted medical lead coupled to the electrical stimulation generator, and a programmer configured to communicate with the electrical stimulation generator. The method comprises communicating first stimulation parameters to the stimulation generator resulting in a first stimulation with the stimulation generator using the first stimulation parameters. The first stimulation parameters include assigned first amplitude values and first polarities for a first set of the electrodes of the plurality of electrodes. The method further comprises determining a discrete migration from the first stimulation parameters to second stimulation parameters in response to a first input and a second input. The determining of the discrete migration includes receiving a first input defining an amount of amplitude change for the migration, receiving a second input defining a direction for the migration, and calculating the second stimulation parameters using the first stimulation parameters, the first input, and the second input. The second stimulation parameters included assigned second amplitude values and second polarities for a second set of the electrodes of the plurality of electrodes. The method also includes communicating the second stimulation parameters to the stimulation generator resulting in cessation of the first stimulation and initiation of a second stimulation with the stimulation generator using the second stimulation parameters.

In another embodiment, the invention provides a programmer for developing a program to provide therapeutic electrical stimulation to a patient with an electrical stimulation generator and an implanted medical lead coupled to the electrical stimulation generator. The programmer comprises a first user-controllable input configured for receiving a first input defining an amount of amplitude change for a discrete stimulus migration, a second user-controllable input configured for receiving a second input defining a direction for the migration, and a processor configured for receiving the first input, receiving the second input, and calculating second stimulation parameters using first stimulation parameters, the first input, and the second input. The first stimulation parameters included assigned first amplitude values and first polarities for a first set of the plurality of electrodes and the second stimulation parameters including assigned second amplitude values and second polarities for a second set of the plurality of electrodes. The programmer also comprises a transmitter configured for communicating the second stimulation parameters to the stimulation generator resulting in cessation of a first stimulation and initiation of a second stimulation with the stimulation generator using the second stimulation parameters.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The invention herein relates to an electrical stimulation system for providing stimulation to target tissue of a patient. The system described in detail below is a spinal cord stimulation (SCS) system for providing electrical pulses to the neurons of the spinal cord of a patient. However, many aspects of the invention are not limited to spinal cord stimulation. The electrical stimulation system may provide stimulation to other body portions including a muscle or muscle group, nerves, the brain, etc.

Figure 1:
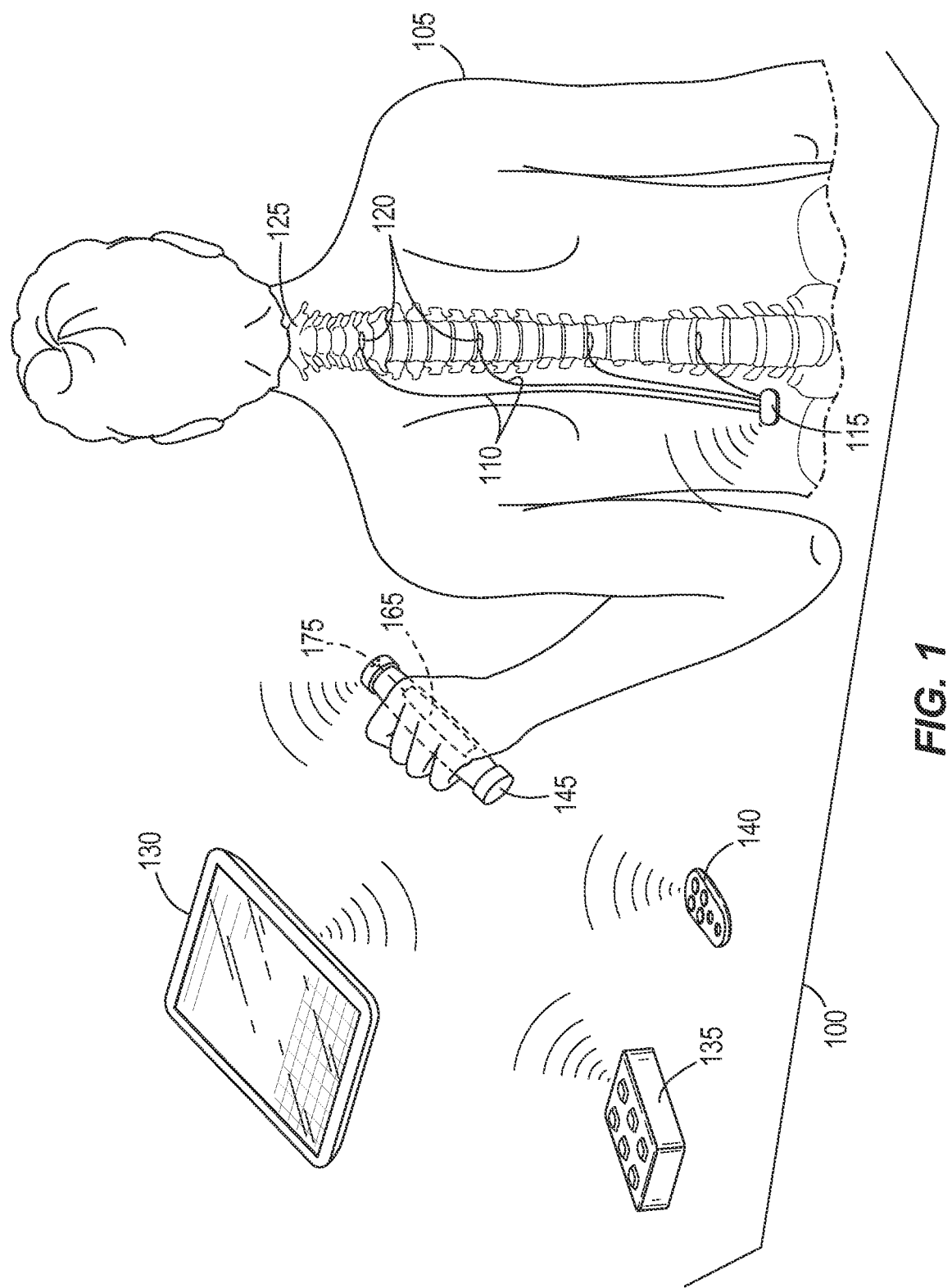
FIG. 1 is a partial perspective view of a patient using a spinal cord stimulation system.

FIG. 1 shows a spinal cord stimulation system 100 in use with a patient 105. The system includes one or more implanted medical electrical leads 110 connected to an implantable pulse generator (IPG) 115. The leads 110 include an electrode array 120 at a distal end of the base lead cable. The electrode array 120 includes one or more electrical stimulation electrodes (may also be referred as electrode contacts or simply electrodes) and is placed adjacent to the dura of the spine using an anchor. The spinal column 125 includes the C1-C7 (cervical), T1-T12 (thoracic), L1-L5 (lumbar) and S1-S6 (sacral) vertebrae and the electrode array(s) 120 may be positioned anywhere along the spine cord to deliver the intended therapeutic effects of spinal cord electrical stimulation in a desired region of the spine. The electrodes (discussed further in FIGS. 2 and 3) of the electrode arrays 120 promote electrical stimulation to the neurons of the spine based on electrical signals generated by the IPG 115. In one construction, the electrical signals are regulated current pulses that are rectangular in shape. However, the electrical signals can be other types of signals, including other types of pulses (e.g., regulated voltage pulses), and other shapes of pulses (e.g., trapezoidal, sinusoidal). The stimulation is provided from the IPG 115 to the electrodes via the base lead, which is connected to the IPG 115 with the proximal end of the base lead. The body of the lead can traverse through the body of the patient via the spinal column and from the spinal column through the body of the patient to the implant site of the IPG 115.

The IPG 115 generates the electrical signals through a multiplicity of electrodes (e.g., four, eight, sixteen, twenty-four electrodes). The IPG 115 can control six aspects of electrical stimulation based on a stimulation program (may also be referred to as a stimulation protocol): on/off, amplitude (e.g., current or voltage), frequency, pulse width, pulse shape, and polarity (e.g., anodic or cathodic stimulation). The stimulation most discussed herein is a regulated (or constant) current that provides square wave stimulation with a variable amplitude, fixed frequency, and fixed pulse width. Typically, the IPG 115 is implanted in a surgically made pocket (e.g., in the abdomen) of the patient. However, the pulse generator can also be an external pulse generator (EPG).

The IPG 115 communicates with any one of a clinician programmer (CP) 130, a patient programmer and charger (PPC) 135, and a pocket (or fob) programmer (PP) 140. As discussed in further detail herein, the CP 130 interacts with the IPG 115 to develop a stimulation program for stimulating the patient. The developing of the program may be assisted with the use of a patient-feedback device (PFD) 145. Once a stimulation program is developed, the PPC 135 or the PP 140 can activate, deactivate, or perform limited changes to the programming parameters of the stimulation program. The stimulation program may be stored at the IPG 115 or can be communicated and stored at the PPC 135 or the PP 140. The PPC 135 is also used for charging the IPG 115.

For the construction described herein, the IPG 115 includes a rechargeable, multichannel, radio-frequency (RF) programmable pulse generator housed in a metallic (e.g., titanium) case or housing. The metallic case is sometimes referred to as the "can" and may act as a cathode or an anode to the electrical contacts or may be "floating" with respect to the electrical contacts.

Figure 2:
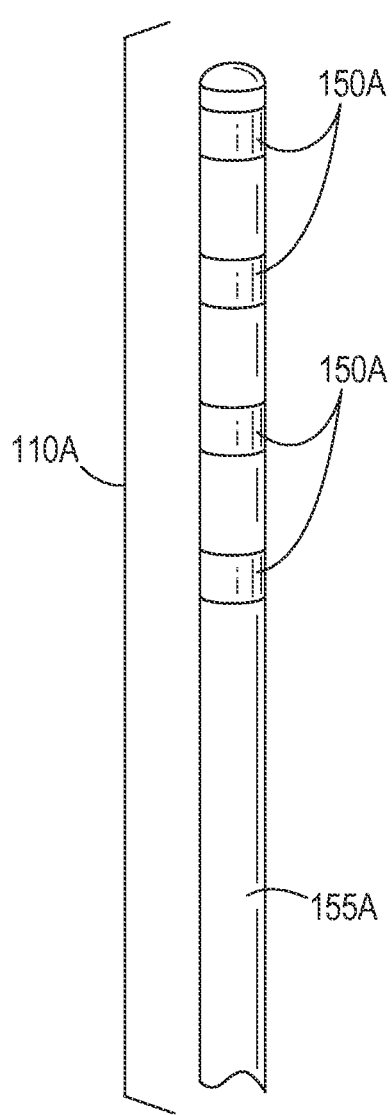
FIG. 2 is a perspective view of an in-line lead for use in the spinal cord stimulation system of FIG. 1.
Figure 3:
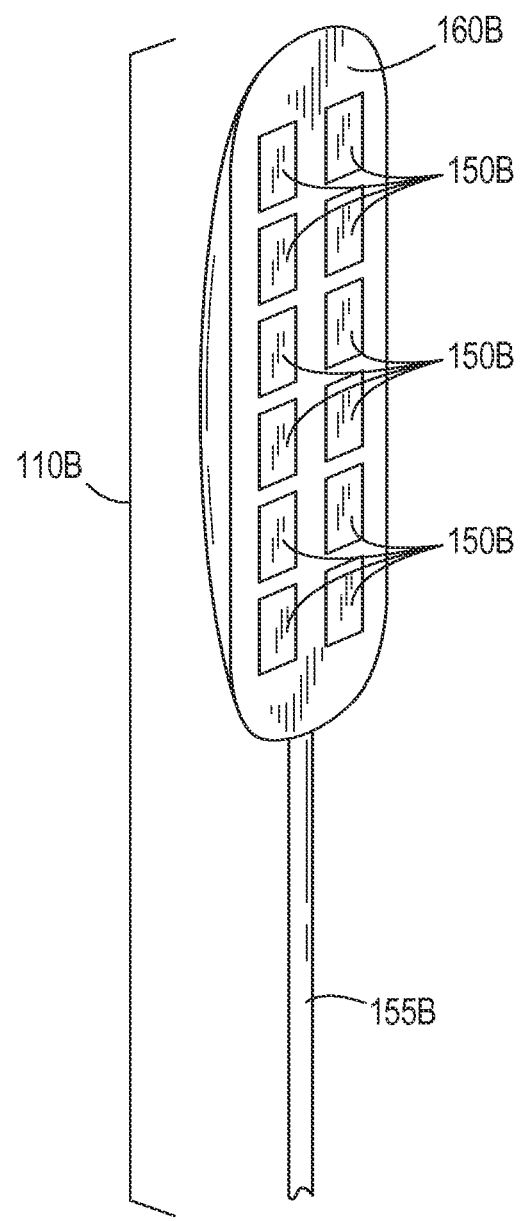
FIG. 3 is a perspective view of a paddle lead for use in the spinal cord stimulation system of FIG. 1.

Referring now to FIGS. 2 and 3, the figures show two exemplary leads 110A and 110B, respectively, that can be used in the SCS system. A first common type of lead is the "in-line" lead 110A shown in FIG. 2. An in-line lead 110A includes individual electrodes 150A along the length of a flexible cable 155A. A second common type of lead 110 is the "paddle" lead shown in FIG. 3. In general, the paddle lead 110B is shaped with a wide platform 160B on which a variety of electrode 150B configurations are situated. For example, the paddle lead 110B shown in FIG. 3 has two columns of six rectangular shaped electrodes 150B. A paddle lead typically contains contacts on one side only, but is not restricted to individual electrodes on either side, or electrodes perforating the carrier material.

For both leads shown in FIGS. 2 and 3, a flexible cable 155A or 155B has respective small wires for the electrodes 150A or 150B. The wires are embedded within the cable 155A or 155B and carry the electrical stimulation from the IPG 115 to the electrodes 150A or 150B.

It is envisioned that other types of leads and electrode arrays can be used with the invention. Also, the number of electrodes and how the electrodes are arranged in the electrode array can vary from the examples discussed herein.

The leads shown in FIGS. 2 and 3 provide for multiple-channel leads. Here, a "channel" is defined as a specified electrode 150, or group of electrodes 150, that receives a specified pattern or sequence of electrical stimuli. For simplicity, this description will focus on each electrode 150 and the IPG's 115 metallic housing providing a respective channel. When more than one channel is available, each channel may be programmed to provide its own stimulus to its defined electrode 150.

There are many instances when it is advantageous to have multiple channels for stimulation. For example, different pain locations (e.g., upper extremities, lower extremities) of the patient may require different stimuli. Further, some patients may exhibit conditions better suited to "horizontal" stimulation paths, while other patients may exhibit conditions better suited to "vertical" stimulation paths. Therefore, multiple electrodes positioned to provide multiple channels can cover more tissue/neuron area, and thereby provide better stimulation program flexibility to treat the patient.

It is also envisioned that the number of leads 110 can vary. For example, one, two, or four leads 110 can be connected to the IPG 115. The electrode arrays 120 of the leads 110, respectively, can be disposed in different vertical locations on the spine 125 with respect to a vertical patient 105, can be disposed horizontally (or "side-by-side") on the spine 125 with respect to a vertical patient 105, or some combination thereof.

In alternative to the IPG 115, the leads 110 can receive electrical stimuli from an external pulse generator (EPG) (also referred to a trial stimulator) through one or more percutaneous lead extensions. An EPG may be used during a trial period.

Referring back to FIG. 1, a patient may provide feedback to the CP 130 with a PFD 145 while the CP 130 develops the stimulation for the IPG 115. The patient 105 might activate the PFD 145 when the patient 105 feels various stimuli, such as paresthesia or pain. In FIG. 1, the PFD 145 is an ergonomic handheld device having a sensor (also referred to as input) 165, a controller, and a communication output 175. The sensor 165 can take the form of a discrete switch or can take the form of a continuously variable input, such as through the use of a strain gauge. It is envisioned that the use of a continuously variable input can provide magnitude information, thereby providing feedback information. Further examples of various patient feedback devices are disclosed in US Patent Application Publication Nos. 2012/0310305 A1, 2012/0310300 A1, and 2012/0310299 A1, all of which are incorporated herein by reference in their entireties.

As discussed earlier, it should be understood that aspects of the SCS system 110 can be applied to other types of electrical stimulation systems. That is, other electrical stimulation systems provide electrical stimuli to other types of target tissues. Similar to the SCS system 110, these other electrical stimulation systems include one or more medical electrical leads having electrodes, a stimulation generator coupled to the one or more medical electrical leads, and a clinician programmer for establishing a program for the stimulation generator.

Figure 4:
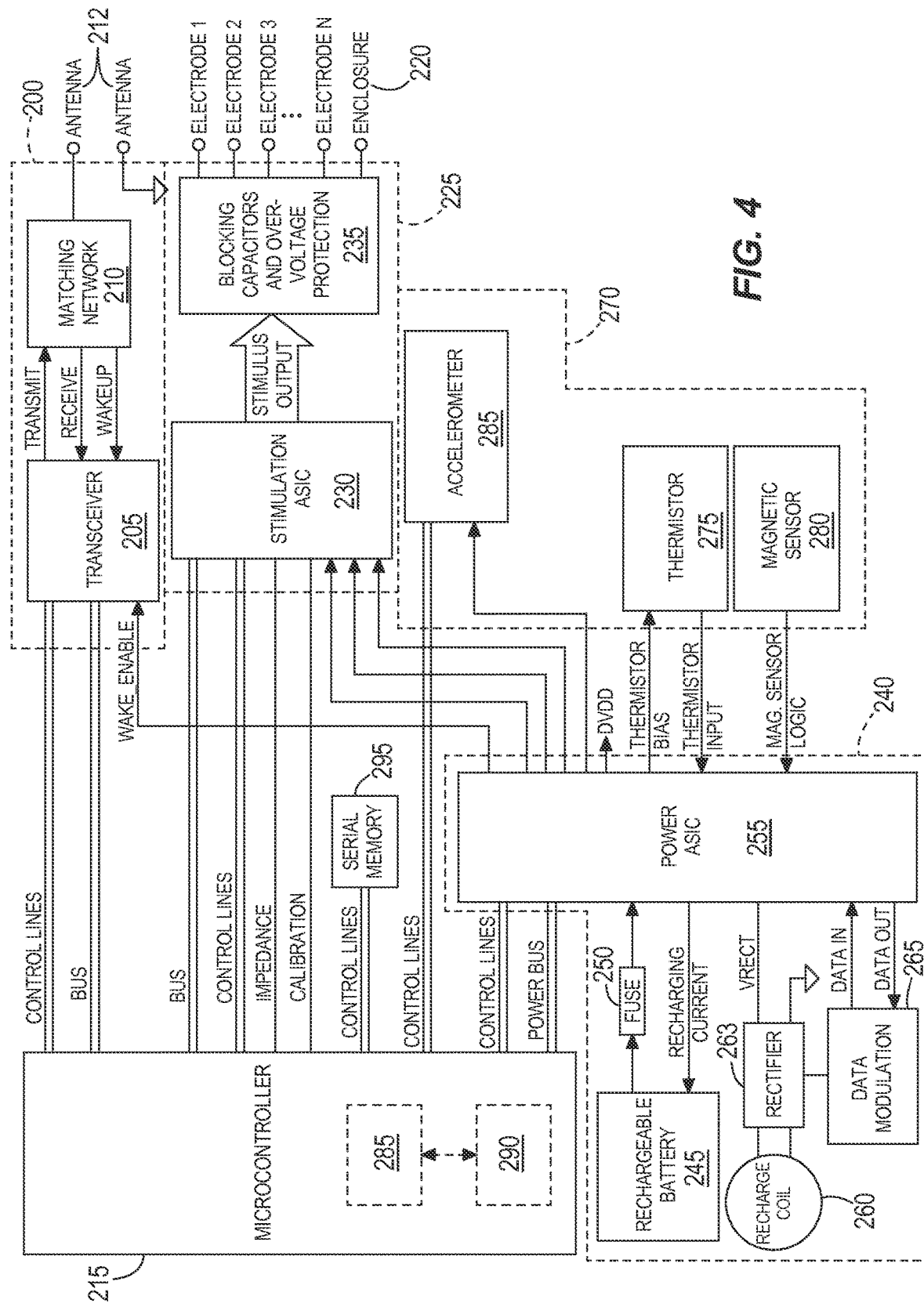
FIG. 4 is a block diagram of the implantable pulse generator of FIG. 1.

FIG. 4 shows a block diagram of one construction of the IPG 115. The IPG 115 includes a printed circuit board ("PCB") that is populated with a plurality of electrical and electronic components that provide power, operational control, and protection to the IPG 115. With reference to FIG. 4, the IPG 115 includes a communication portion 200 having a transceiver 205, a matching network 210, and an antenna 212. The communication portion 200 receives power from a power ASIC (discussed below), and communicates information to/from the microcontroller 215 and a device (e.g., the CP 130) external to the IPG 115. For example, the IPG 115 can provide bi-direction radio communication capabilities, including Medical Implant Communication Service (MICS) bi-direction radio communication following the MICS specification.

The IPG 115, as already discussed, provides stimuli to electrodes 150 of an implanted medical electrical lead 110. As shown in FIG. 4, N electrodes 150 are connected to the IPG 115. In addition, the enclosure or housing 220 of the IPG 115 can act as an electrode. The stimuli are provided by a stimulation portion 225 in response to commands from the microcontroller 215. The stimulation portion 225 includes a stimulation application specific integrated circuit (ASIC) 230 and circuitry including blocking capacitors and an over-voltage protection circuit. As is well known, an ASIC is an integrated circuit customized for a particular use, rather than for general purpose use. ASICs often include processors, memory blocks including ROM, RAM, EEPROM, Flash, etc. The stimulation ASIC 230 can include a processor, memory, and firmware for storing preset pulses and protocols that can be selected via the microcontroller 215. The providing of the pulses to the electrodes 150 is controlled through the use of a waveform generator and amplitude multiplier of the stimulation ASIC 230, and the blocking capacitors and overvoltage protection circuitry of the stimulation portion 225, as is known in the art. The stimulation portion 225 of the IPG 115 receives power from the power ASIC (discussed below). The stimulation ASIC 230 also provides signals to the microcontroller 215. More specifically, the stimulation ASIC 230 can provide impedance values for the channels associated with the electrodes 150, and also communicate calibration information with the microcontroller 215 during calibration of the IPG 115.

The IPG 115 also includes a power supply portion 240. The power supply portion includes a rechargeable battery 245, fuse 250, power ASIC 255, recharge coil 260, rectifier 263 and data modulation circuit 265. The rechargeable battery 245 provides a power source for the power supply portion 240. The recharge coil 260 receives a wireless signal from the PPC 135. The wireless signal includes an energy that is converted and conditioned to a power signal by the rectifier 263. The power signal is provided to the rechargeable battery 245 via the power ASIC 255. The power ASIC 255 manages the power for the IPG 115. The power ASIC 255 provides one or more voltages to the other electrical and electronic circuits of the IPG 155. The data modulation circuit 265 controls the charging process.

The IPG also includes a magnetic sensor 280. The magnetic sensor 280 provides a "hard" switch upon sensing a magnet for a defined period. The signal from the magnetic sensor 280 can provide an override for the IPG 115 if a fault is occurring with the IPG 115 and is not responding to other controllers.

The IPG 115 is shown in FIG. 4 as having a microcontroller 215. Generally speaking, the microcontroller 215 is a controller for controlling the IPG 115. The microcontroller 215 includes a suitable programmable portion 285 (e.g., a microprocessor or a digital signal processor), a memory 290, and a bus or other communication lines. An exemplary microcontroller capable of being used with the IPG is a model MSP430 ultra-low power, mixed signal processor by Texas Instruments. More specifically, the MSP430 mixed signal processor has internal RAM and flash memories, an internal clock, and peripheral interface capabilities. Further information regarding the MSP 430 mixed signal processor can be found in, for example, the "MSP430G2x32, MSP430G2x02 MIXED SIGNAL MICROCONTROLLER" data sheet; dated December 2010, published by Texas Instruments at its website; the content of the data sheet being incorporated herein by reference.

The IPG 115 includes memory, which can be internal to the control device (such as memory 290), external to the control device (such as serial memory 295), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The programmable portion 285 executes software that is capable of being stored in the RAM (e.g., during execution), the ROM (e.g., on a generally permanent basis), or another non-transitory computer readable medium such as another memory or a disc.

Software included in the implementation of the IPG 115 is stored in the memory 290. The software includes, for example, firmware, one or more applications, program data, one or more program modules, and other executable instructions. The programmable portion 285 is configured to retrieve from memory and execute, among other things, instructions related to the control processes and methods described below for the IPG 115. For example, the programmable portion 285 is configured to execute instructions retrieved from the memory 290 for providing stimulation to the electrodes 150 in response to a communicated program from the CP 130.

The PCB also includes a plurality of additional passive and active components such as resistors, capacitors, inductors, integrated circuits, and amplifiers. These components are arranged and connected to provide a plurality of electrical functions to the PCB including, among other things, filtering, signal conditioning, or voltage regulation, as is commonly known.

Figure 5:
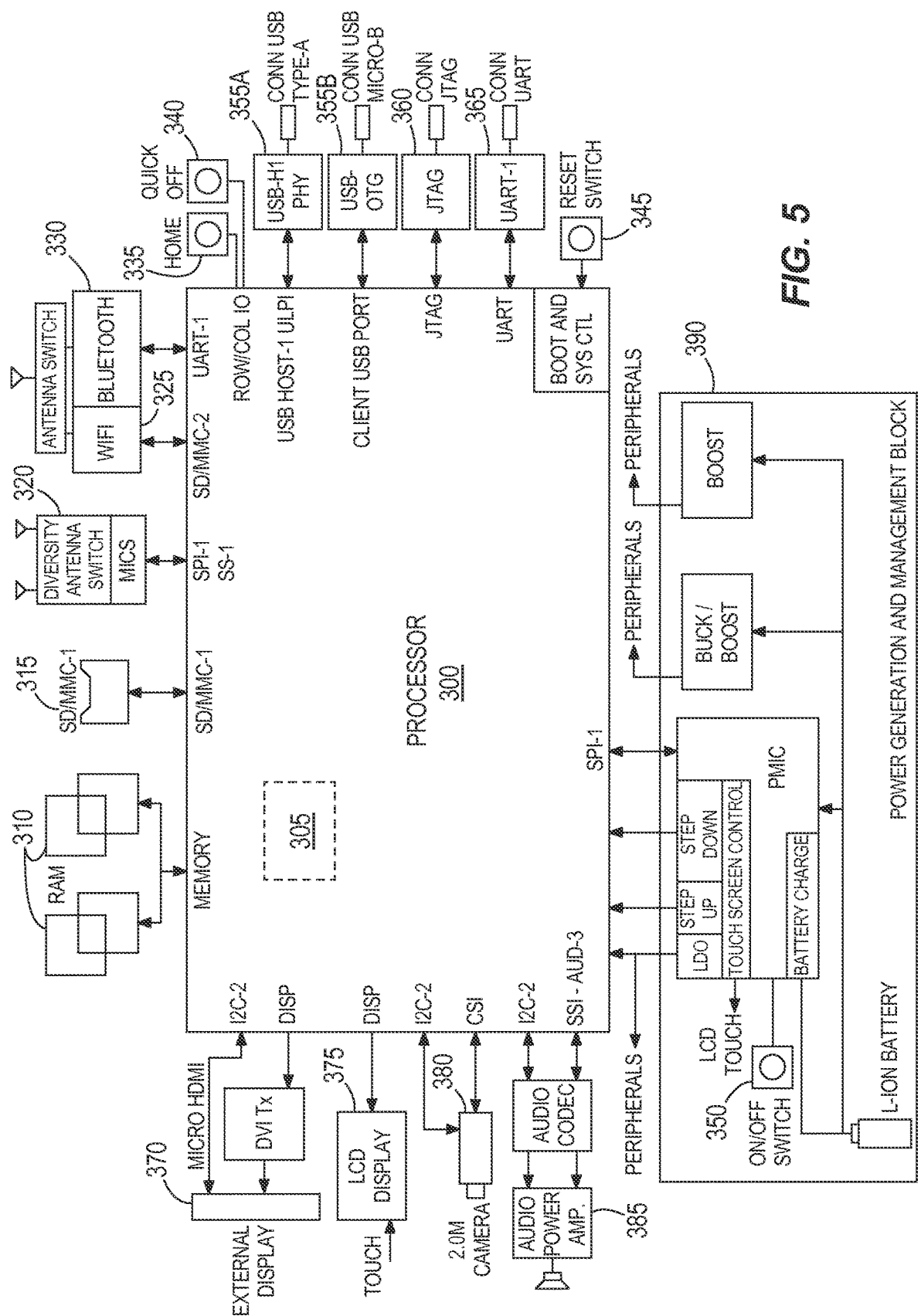
FIG. 5 is a block diagram of a clinician programmer of FIG. 1.

FIG. 5 shows a block diagram of one construction of the CP 130. The CP 130 includes a printed circuit board ("PCB") that is populated with a plurality of electrical and electronic components that provide power, operational control, and protection to the CP 130. With reference to FIG. 5, the CP includes a processor 300. The processor 300 is a controller for controlling the CP 130 and, indirectly, the IPG 115 as discussed further below. In one construction, the processor 300 is an applications processor model i.MX515 available from Freescale Semiconductor. More specifically, the i.MX515 applications processor has internal instruction and data cashes, multimedia capabilities, external memory interfacing, and interfacing flexibility. Further information regarding the i.MX515 applications processor can be found in, for example, the "IMX510EC, Rev. 4" data sheet; dated August 2010; published by Freescale Semiconductor at its website, the content of the data sheet being incorporated herein by reference. Of course, other processing units, such as other microprocessors, microcontrollers, digital signal processors, etc., can be used in place of the processor 300.

The CP 130 includes memory, which can be internal to the processor 300 (e.g., memory 305), external to the processor 300 (e.g., memory 310), or a combination of both. Exemplary memory include a read-only memory ("ROM"), a random access memory ("RAM"), an electrically erasable programmable read-only memory ("EEPROM"), a flash memory, a hard disk, or another suitable magnetic, optical, physical, or electronic memory device. The processor 300 executes software that is capable of being stored in the RAM (e.g., during execution), the ROM (e.g., on a generally permanent basis), or another non-transitory computer readable medium such as another memory or a disc. The CP 130 also includes input/output ("I/O") systems that include routines for transferring information between components within the processor 300 and other components of the CP 130 or external to the CP 130.

Software included in the implementation of the CP 130 is stored in the memory 305 of the processor 300, RAM 310, ROM 315, or external to the CP 130. The software includes, for example, firmware, one or more applications, program data, one or more program modules, and other executable instructions. The processor 300 is configured to retrieve from memory and execute, among other things, instructions related to the control processes and methods described below for the CP 130. For example, the processor 300 is configured to execute instructions retrieved from the memory 140 for establishing a protocol to control the IPG 115.

One memory shown in FIG. 5 is memory 310, which can be a double data rate (DDR2) synchronous dynamic random access memory (SDRAM) for storing data relating to and captured during the operation of the CP 130. In addition, a secure digital (SD) multimedia card (MMC) can be coupled to the CP for transferring data from the CP to the memory card via slot 315. Of course, other types of data storage devices can be used in place of the data storage devices shown in FIG. 5.

The CP 130 includes multiple bi-directional radio communication capabilities. Specific wireless portions included with the CP 130 are a Medical Implant Communication Service (MICS) bi-direction radio communication portion 320, a WiFi bi-direction radio communication portion 325, and a Bluetooth bi-direction radio communication portion 330. The MICS portion 320 includes a MICS communication interface, an antenna switch, and a related antenna, all of which allows wireless communication using the MICS specification. The WiFi portion 375 and Bluetooth portion 330 include a WiFi communication interface, a Bluetooth communication interface, an antenna switch, and a related antenna all of which allows wireless communication following the WiFi Alliance standard and Bluetooth Special Interest Group standard. Of course, other wireless local area network (WLAN) standards and wireless personal area networks (WPAN) standards can be used with the CP 130.

The CP 130 includes three hard buttons: a "home" button 335 for returning the CP to a home screen for the device, a "quick off" button 340 for quickly deactivating stimulation IPG, and a "reset" button 345 for rebooting the CP 130. The CP 130 also includes an "ON/OFF" switch 350, which is part of the power generation and management block (discussed below).

The CP 130 includes multiple communication portions for wired communication. Exemplary circuitry and ports for receiving a wired connector include a portion and related port for supporting universal serial bus (USB) connectivity 355, including a Type-A port and a Micro-B port; a portion and related port for supporting Joint Test Action Group (JTAG) connectivity 360, and a portion and related port for supporting universal asynchronous receiver/transmitter (UART) connectivity 365. Of course, other wired communication standards and connectivity can be used with or in place of the types shown in FIG. 5.

Another device connectable to the CP 130, and therefore supported by the CP 130, is an external display. The connection to the external display can be made via a micro High-Definition Multimedia Interface (HDMI) 370, which provides a compact audio/video interface for transmitting uncompressed digital data to the external display. The use of the HDMI connection 370 allows the CP 130 to transmit video (and audio) communication to an external display.

The CP 130 includes a touch screen I/O device 375 for providing a user interface with the health care professional (HCP). The touch screen display 375 can be a liquid crystal display (LCD) having a resistive, capacitive, or similar touch-screen technology. It is envisioned that multitouch capabilities can be used with the touch screen display 375 depending on the type of technology used.

The CP 130 includes a camera 380 allowing the device to take pictures or video. The resulting image files can be used to document a procedure or an aspect of the procedure. For example, the camera 380 can be used to take pictures of barcodes associated with the IPG 115 or the leads 120, or documenting an aspect of the procedure, such as the positioning of the leads. Similarly, it is envisioned that the CP 130 can communicate with a fluoroscope or similar device to provide further documentation of the procedure. Other devices can be coupled to the CP 130 to provide further information, such as scanners or RFID detection. Similarly, the CP 130 includes an audio portion 385 having an audio codec circuit, audio power amplifier, and related speaker for providing audio communication to the user, such as a clinician or surgeon.

The CP 130 further includes a power generation and management block 390. The power block 390 has a power source (e.g., a lithium-ion battery) and a power supply for providing multiple power voltages to the processor, LCD touch screen, and peripherals.

As best shown in FIG. 1, the CP 130 can be a handheld computing tablet with touch screen capabilities and an application implemented by the tablet. The tablet is a portable personal computer with a touch screen, which is typically the primary input device. However, an external keyboard or mouse can be attached to the CP 130. The tablet allows for mobile functionality not associated with even typical laptop personal computers.

In operation, the IPG 115 (or alternatively the EPG) through the use of the implanted medical electrical leads 110, and specifically the electrodes 150, stimulates neurons of the spinal cord 125. The IPG 115 selects an electrode stimulating configuration, selects a stimulation waveform, regulates the amplitude of the electrical stimulation, controls the width and frequency of electrical pulses, and selects cathodic, anodic, or bi-phasic stimulation. This is accomplished by the HCP, using the CP 130, setting the parameters of the IPG 115. The setting of parameters of the IPG results from a stimulation program, which may also be referred to as a "protocol," for the electrode stimulation. Programming may result in multiple stimulation programs that the patient can choose from. Multiple stimulation programs allow, for example, the patient to find a best setting for paresthesia at a particular time of treatment.

With reference to FIG. 3, an electrode array includes twelve electrodes 150B. The shown electrode array has two columns and six rows as viewed along a longitude length of the lead 110. More generically, the lead includes cl columns and r rows, where cl is two and r is six. When referring to a particular column, the column is referred to herein as the j-th column, and when referring to a particular row, the row is referred to as the i-th row.

Before proceeding further, it should be understood that not all electrode arrays are conveniently shaped as a simple matrix having definite columns and definite rows. More complex configurations are possible, which are referred to herein as complex electrode array configurations. Also, multiple leads can be grouped together to "form" a single complex electrode array. The processes discussed herein can account for complex electrode array configurations. For example, a representative array having cl columns and r rows for a complex electrode array configuration may include "dummy" addresses having "null" values in the array. For a specific example, an electrode contact may span multiple columns. The resulting array may have a first address i, j representing the multiple column electrode and a second address i, j+1 having a "null" value to account for the multiple columns of the multiple column electrode. This concept can be expanded to even more complex arrangements. Accordingly, all electrode arrays 120, including multiple lead arrays, can be addressed as a matrix and it will be assumed herein that the electrode array 120 has been addressed as a matrix.

There are numerous processes of determining a program for providing electrical stimulation. Some exemplary processes are disclosed in US Patent Application Publication Nos. 2012/0310305 A1 and 2012/0310300 A1, both of which are already incorporated herein by reference in their entirety. Other exemplary processes are discussed in detail below.

Before proceeding further, it should be understood that the steps discussed herein will be discussed in an iterative manner for descriptive purposes. Various steps described herein with respect to the processes are capable of being executed in an order that differs from the illustrated serial and iterative manner of discussion. It is also envisioned that not all steps are required as described below.

The patient 105 performs a visit with a health care professional (HCP). While performing the visit, the HCP controls the IPG 115 using the CP 130 to capture implant information, group leads, assign stimulation parameters, and migrate parameters to neighboring electrodes. The HCP starts working with the patient 105 by logging into the CP 130, and either selects a stored existing patient or adds a new patient to the CP 130. It is assumed that the lead 110 is already placed in the patient 105 and the electrode array is attached to the patient's spinal cord.

When capturing implant information, lead identifications and their respective locations are recorded in the CP 130. The camera 380 may be used to capture images of the procedure, and capture/read barcode serial numbers of the leads 110. It also envisioned that fluoroscopy/X-ray images can be recorded in the CP 130 as part of the surgical procedure. The result is that the CP 130 has a type, location, orientation, and other contextual information relating to the implanting of the lead 110. The CP 130 also provides an interface to the HCP that allows the HCP to group multiple leads according to their implanted positions. The capturing of the implant information allows the CP 130 to construct a spatial relationship that can be used to capture a representation of electrodes and their respective position within the spinal column. Also, the captured information can assist the HCP migrate configured parameters toward a desired location. The purpose is that electrodes that are adjacent to each other and connected to the same pulse generator 115 can shift stimulation amplitude amongst each other.

FIGS. 6-9 provide partial screen images of a touch screen of the CP 130. The HCP can manipulate the placement of the leads, and more specifically electrode arrays, with respect to the spinal cord/column 505/510. FIGS. 6-9 illustrate multiple examples of implants captured by the CP 130. FIGS. 6-9 also show the spatial relationship between leads and electrodes.

Figure 6:
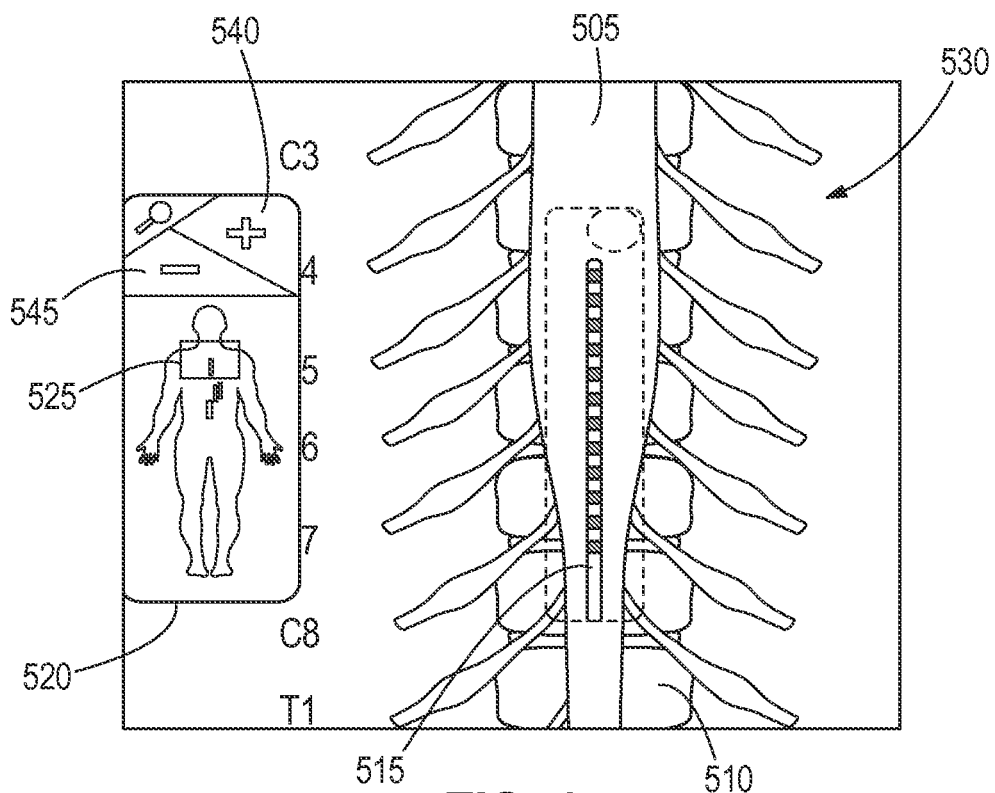
FIGS. 6-13 are partial screen images of a touch screen of the clinician programmer of FIG. 1.
Figure 7:
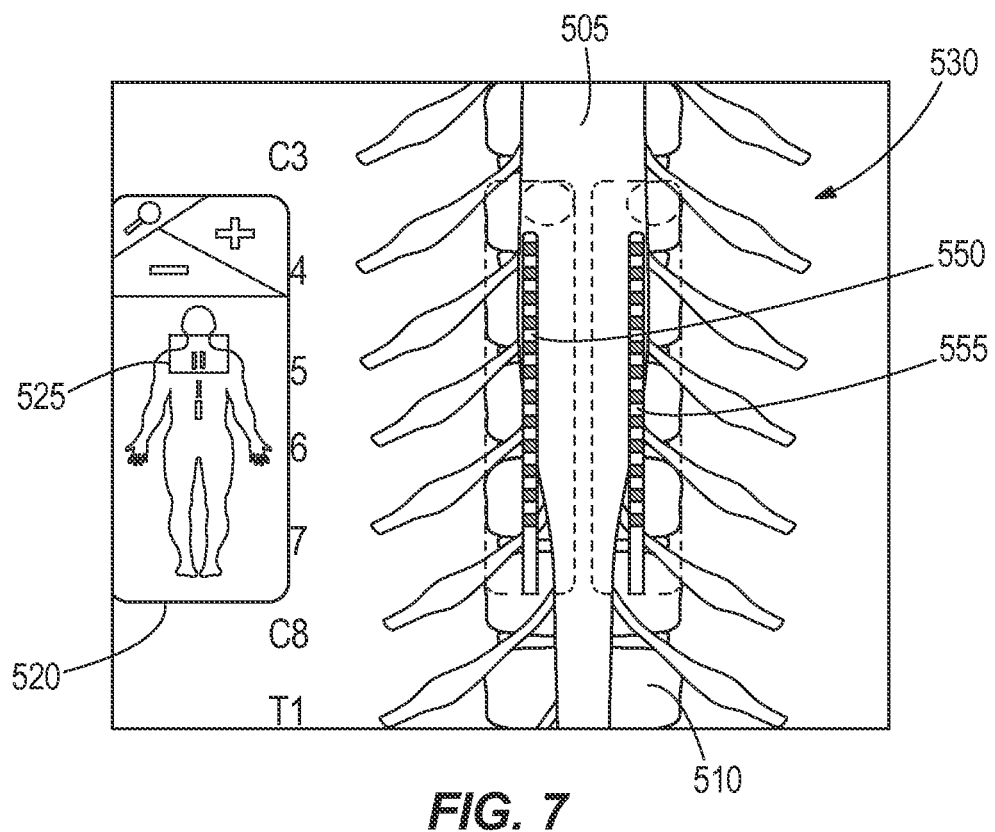
Figure 8:
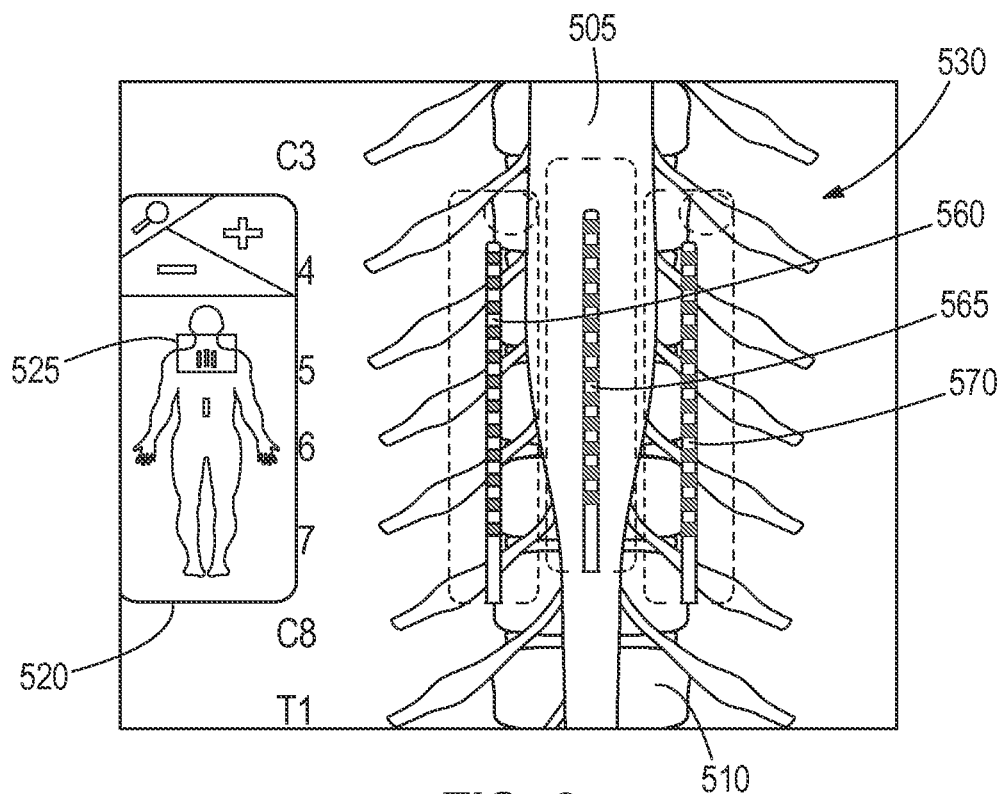
Figure 9:
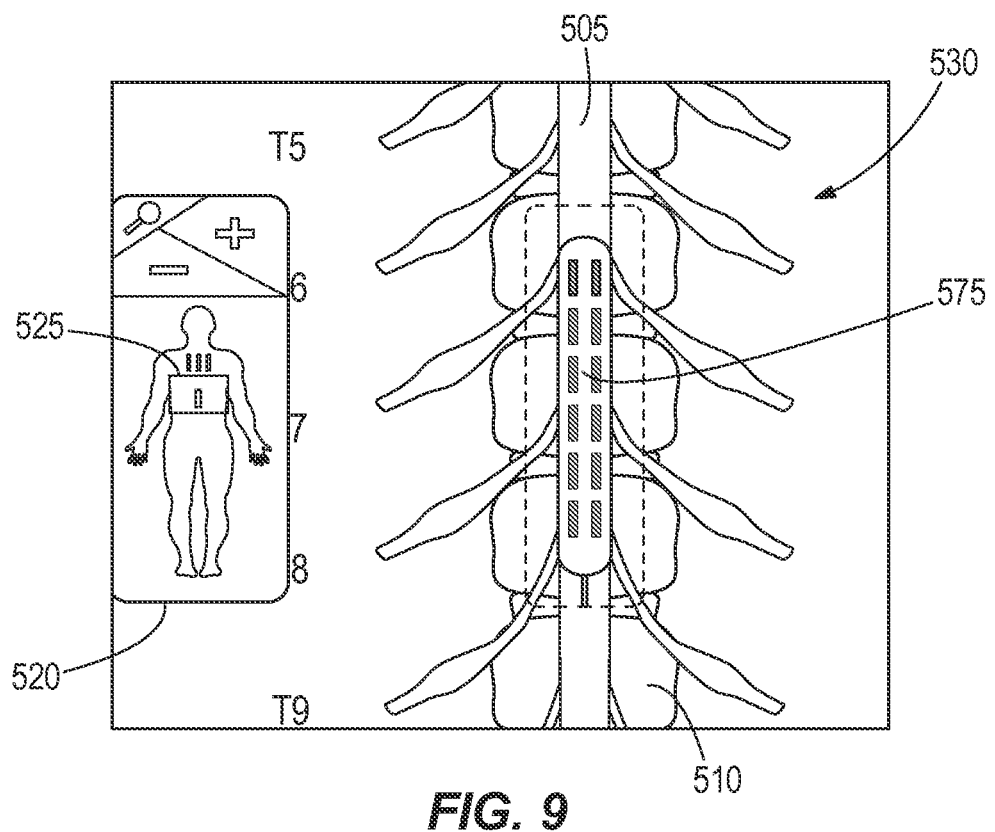

For example, FIG. 6 shows a single percutaneous lead 515 configured with no other leads. The pane 520 includes a window 525 indicating a zoomed portion 530 of the spinal column 510. The zoomed portion is a partial image of the anatomical representation of the spinal cord 505 and spinal column 510 with a partial virtual representation of the location of the lead 515 with respect to the spinal cord/column 505/510. All of FIGS. 6-9 include the pane 520 and the zoom window 525. The zoom window 525 can be increased and decreased with icons 540 and 545. In FIG. 6, the lead is located between C5 and T1 of the spinal column 510. FIG. 7 shows portions of two percutaneous leads 550 and 555 to be programmed as a group. FIG. 8 shows portions of three percutaneous leads 560, 565, and 570 to be programmed as a group. FIG. 9 shows a portion of a single paddle lead 575.

After the HCP captures or selects a representation of the implants with the CP 130, the HCP, with the assistance of the patient, assigns initial programming parameters. The programming may be via a computer assisted stimulation programming (CASP) process, such as described in US Patent Application Publication Nos. 2012/0310305 A1 and 2012/0310300 A1, or may be via a manual process.

With computer assisted programming, the CP 130 establishes an initial stimulation program for providing electrical stimuli to the patient 105. In the CASP processes discussed in US Patent Application Publication Nos. 2012/0310305 A1 and 2012/0310300 A1, the assisted programming first performs three sweeps of the electrodes 150 to result in a best selection of the electrodes 150 for providing paresthesia. The first sweep is an impedance sweep to determine respective impedances between the IPG 115, connected lead, each electrode, and tissue. The impedances are displayed on the touch screen 375 and can be used by the clinician to help determine whether an electrode falls in between an accepted impedance range. The second sweep is a perception-threshold sweep to find the minimum threshold stimulation sensed by the patient 105 for each electrode. In one implementation, the stimulation sensed by the patient 105 for each electrode 150 is cathodal polarity with the can of the IPG 115 being the anode. For an EPG, a reference electrode may be used in place of the can electrode. The values of the perception-threshold sweep are used to normalize the initial sensation felt by the patient with each electrode 150. The last sweep is a pain-area sweep to identify the optimal paresthesia electrodes to the pain area. Even more accurately, the pain-area sweep eliminates contacts not reaching the pain area. The clinician can then repeat any of the sweeps and/or refine the paresthesia to the patient. The refining of the paresthesia can include adjusting parameters of electric stimulation through the electrodes 150 identified in a set, surrounding an electrode identified in a set with anode or cathode blocks, or migrating a pattern longitudinally or laterally. Further discussion regarding portions of the refinement process will be discussed below.

FIGS. 10-13 provide partial screen images of a touch screen of the CP 130. FIGS. 10-13 illustrate a manual programming process where the controls are provided to the HCP. With manual programming, the HCP selects the necessary electrodes, assigns a stimulation polarity to one or more of the electrodes, manually adjusts pulse amplitude, selects the desired frequency, and selects the pulse width of the electrical stimuli. The HCP can then start the stimulation.

Figure 10:
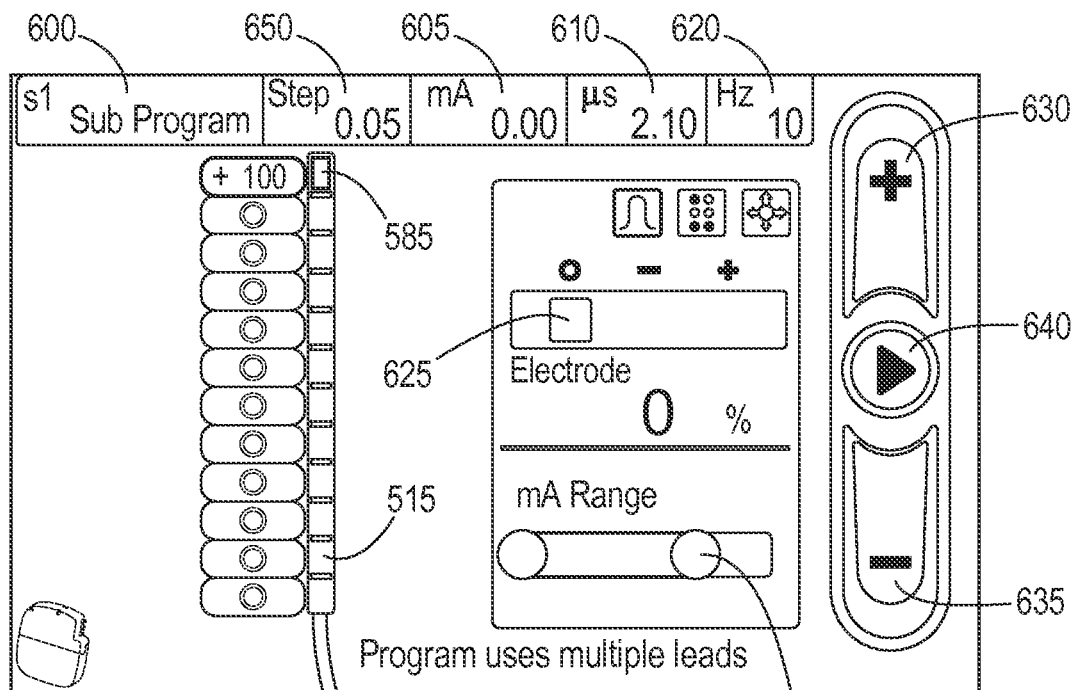
Figure 11:
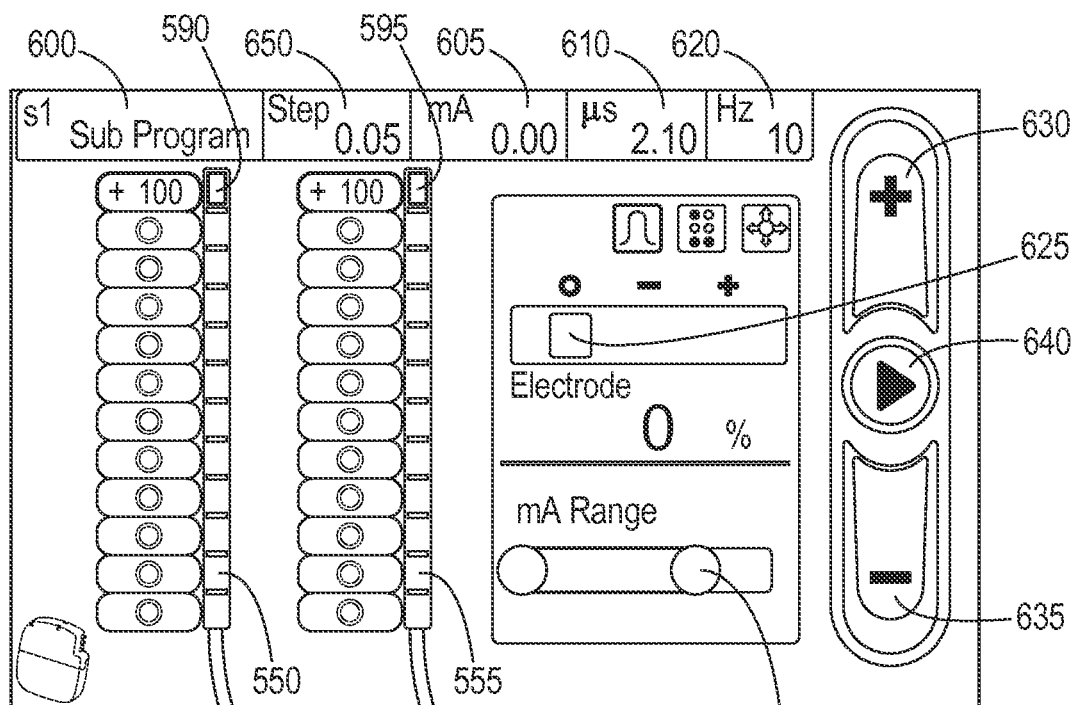
Figure 12:
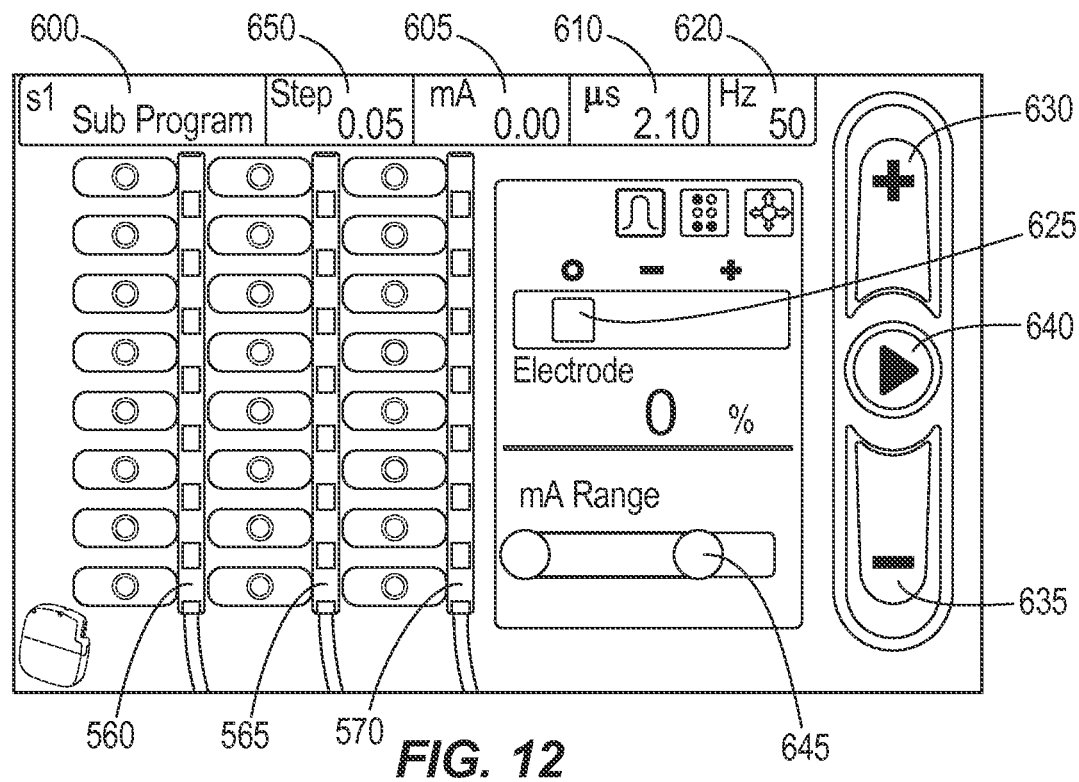

For example, FIG. 10 is a screen image of a single percutaneous lead 515 with the first electrode 585 providing all cathodic stimulation. FIG. 11 is a partial screen image of two percutaneous leads 550 and 555 with the first electrode 590 of the first lead 550 providing one hundred percent cathodic stimulation and the first electrode 595 of the second lead 555 providing one hundred percent anodic stimulation. The percent values are with respect to a normalized maximum amplitude value. For example, if the normalized maximum amplitude value is 7.0 mA for electrode 590, then +100 corresponds to the full anodic pulse amplitude of 7.0 mA. It is envisioned that different ranges can be used (e.g., −10 to +10) or the actual amplitude value can be shown.

Referring again to FIG. 10, the image includes the current program name 600, a program amplitude 605, a step size increment 610, a pulse width 615, and a frequency 620, all of which can be changed or controlled by the HCP. The HCP can select an electrode by touching the electrode (e.g., electrode 585) via the touch screen, identify whether the electrode is cathodic or anodic using the selector 625, increase or decrease values using the icons 630 and 635, and initiate stimulation using the icon 640. The HCP can also program an amplitude range using icon 645 and a step size 650 for changing the current amplitude.

When initiating stimulation with icon 640, the assigned stimulation parameters for the electrodes entered via the touch screen 375 are communicated from the CP 130 to the IPG 115 in the form of a stimulation program. In one construction, the IPG receives the new program, ceases the existing program being run, if any, and initializes and starts the newly received program. The program may run for a defined time period, may be stopped by the HCP via the CP, or cease upon receipt of a new stimulation program.

Figure 14:
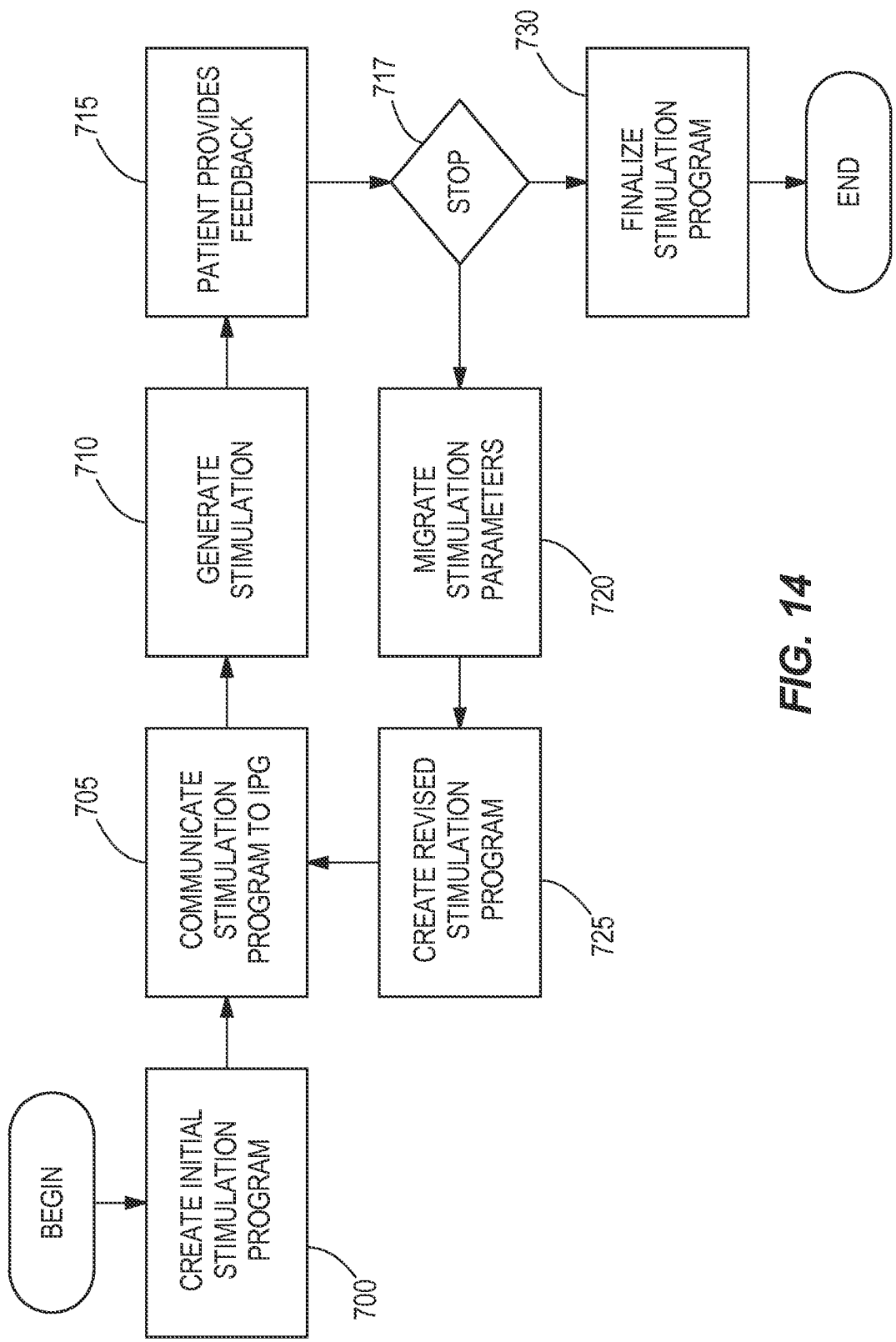
FIG. 14 is a flow diagram of a refinement process.

Once the HCP has captured the initial stimulation program, refinement can be made to the stimulation program resulting in the desired therapy. Based on feedback from the user, the HCP adjusts any of the parameters with the CP 130. A flow chart for the refinement process is shown in FIG. 14.

At block 700, the initial stimulation program is established using the manual or automatic processes discussed above. The HCP then controls the CP 130 to transmit (block 705) the initial stimulation program to the IPG 115, which generates stimulation (block 710) based on the stimulation program. The patient provides feedback (block 715) to the HCP, including whether the stimulation program is satisfactory (block 717). If not and based on the patient's feedback, the HCP makes refinements accordingly (block 720). The HCP beings to adjust stimulation parameters as discussed below. The result of the adjustment is a revised stimulation program (block 725), which is transmitted (block 705) to the IPG 115. The program results in revised stimulation (block 710). The patient provides feedback (block 715), including whether to stop the stimulation refinement process (block 717). If the current stimulation program is satisfactory, then the stimulation is finalized and saved (block 730). If not, the process can be repeated until a stimulation program is deemed satisfactory.

Multiple types of migration controls can be used with the touch screen 130. In one implementation, directional arrows are provided for the HCP to choose the direction of the discrete electrode parameters migration. In another embodiment, a 'joystick-like' control is provided for the HCP to choose any direction through manipulation of the virtual joystick. Other types of user input may be provided to the user, e.g. accelerometers, foot-pedals, motion sensors, keypads and keyboards, pointing devices, track pads, etc.

In FIGS. 15-21, multiple migrating examples are provided. In one implementation (FIGS. 15 and 16), a coarse parameter migration is shown. The coarse parameter migration provides faster discretized parameter migration. In this implementation, the entire set configuration is discretely moved into the direction specified by the HCP. For the example of FIGS. 15 and 16, the HCP selected an upwards migration for target set of electrodes.

Figure 13:
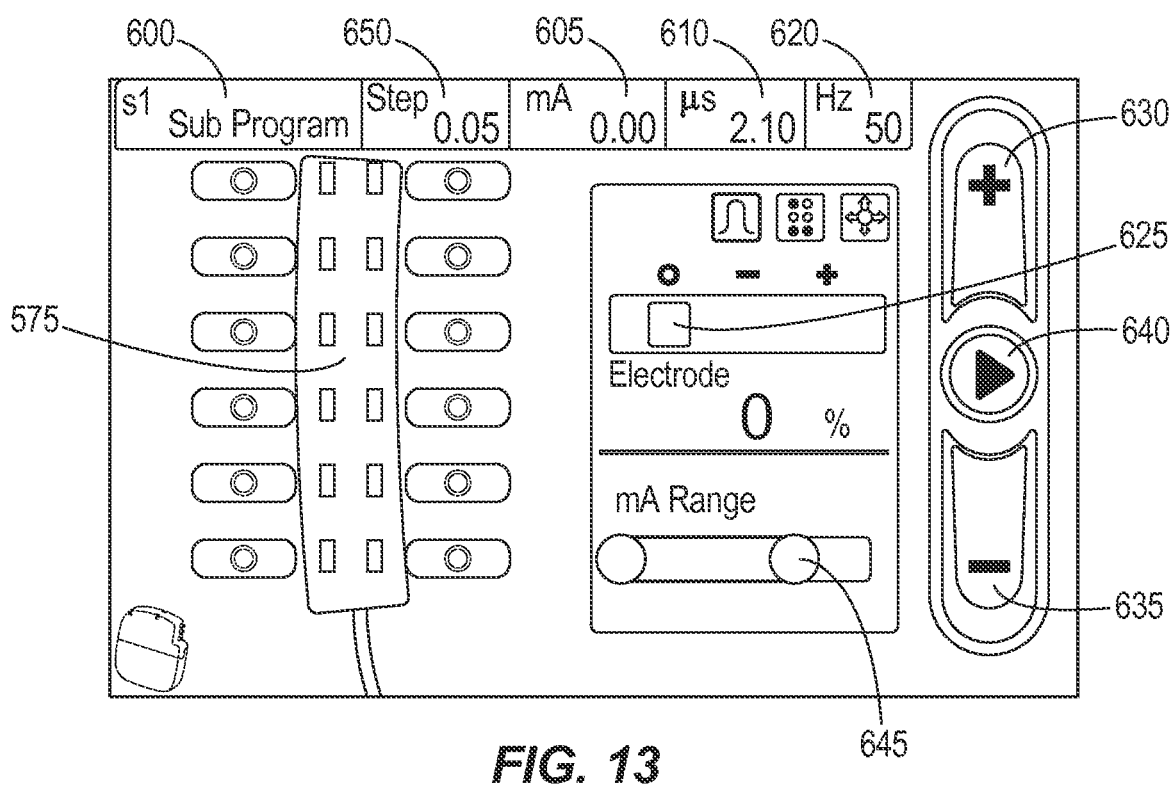
Figure 15:
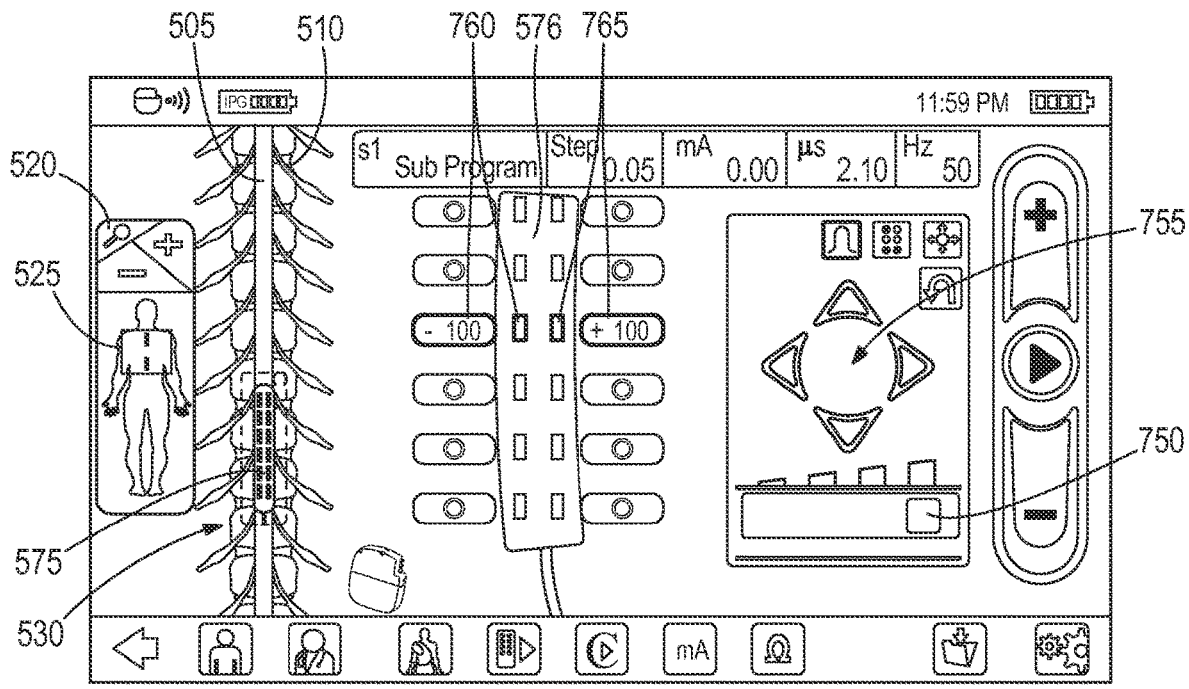
FIGS. 15-21 are screen images of a touch screen of the clinician programmer of FIG. 1.
Figure 16:
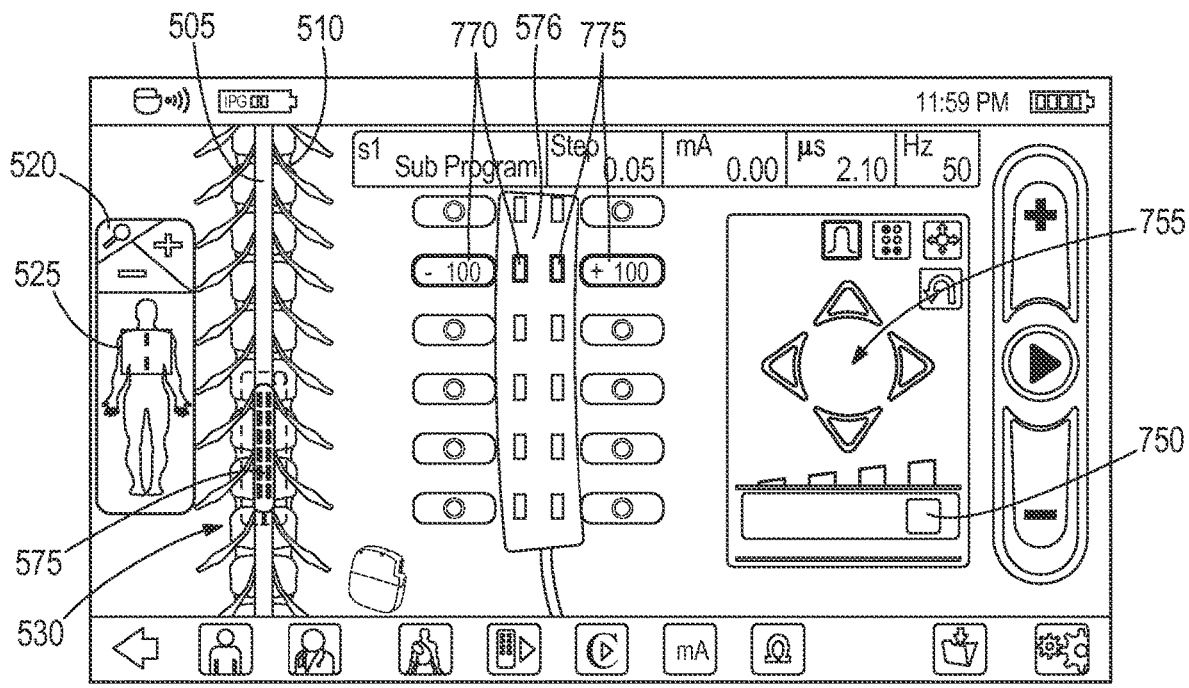

With specific reference to FIG. 15, a screen image is provided with an enlargement pane 520 (as previously discussed in FIGS. 6-9), a partial anatomical representation of a spinal cord/column 505/510 with a lead 575 placed on the representation (as previously discussed in FIG. 9), and an exploded virtual representation of the electrode array 575 with electrode stimulation information associated with the array 576 (as previously discussed in FIG. 13). The screen image also includes a first user-controllable input 750 configured for receiving a first input that defines an amount of amplitude change for a discrete stimulus migration, and a second user-controllable input 755 configured for receiving a second input defining a direction for the migration. The first user-controlled input 750 is referred to herein as a migration discretized amount selector. In FIGS. 15 and 16, the first user-controlled input 750 is set to its maximum setting of 100%. This means that the migration configuration moves one set of electrodes in response to a directional input. So, for example, configuration for electrodes 760 and 765 move up one set of electrodes 770 and 775 in response to an up input 780.

Figure 17:
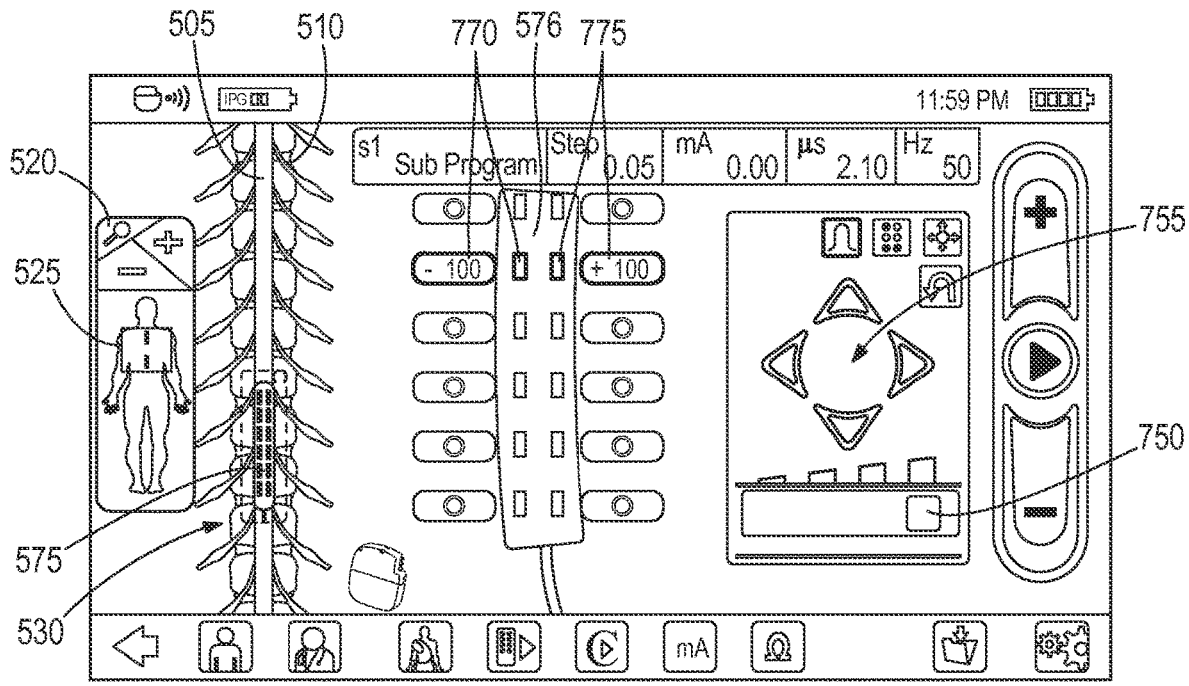
Figure 18:
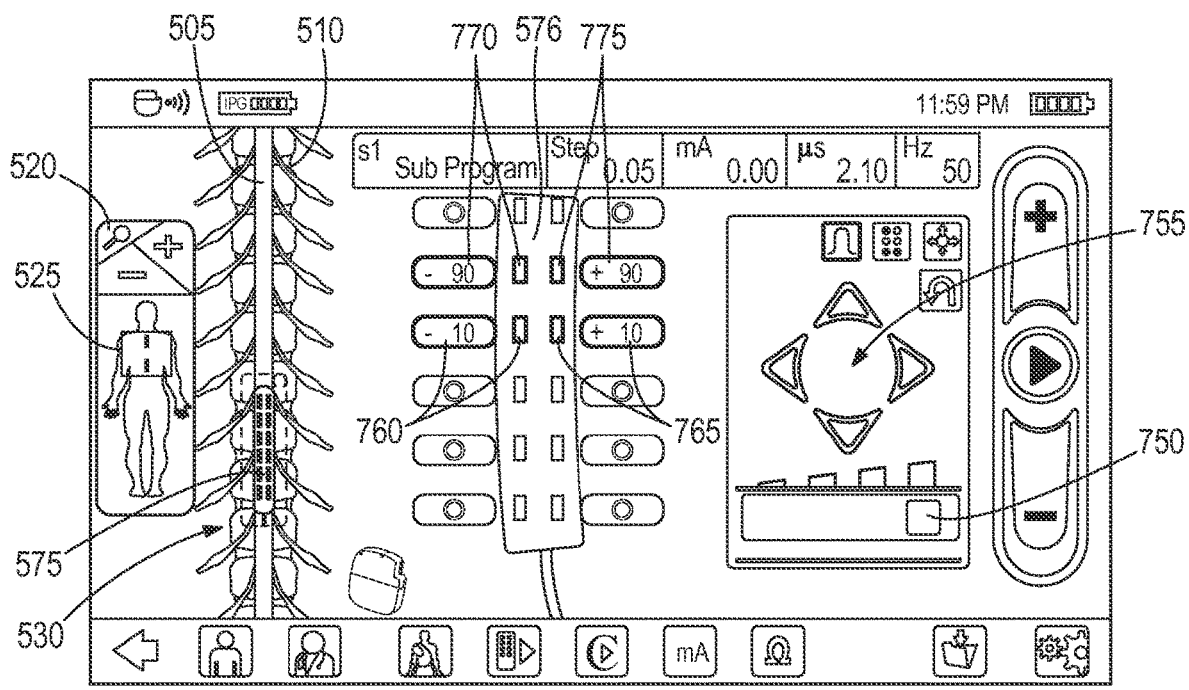
Figure 19:
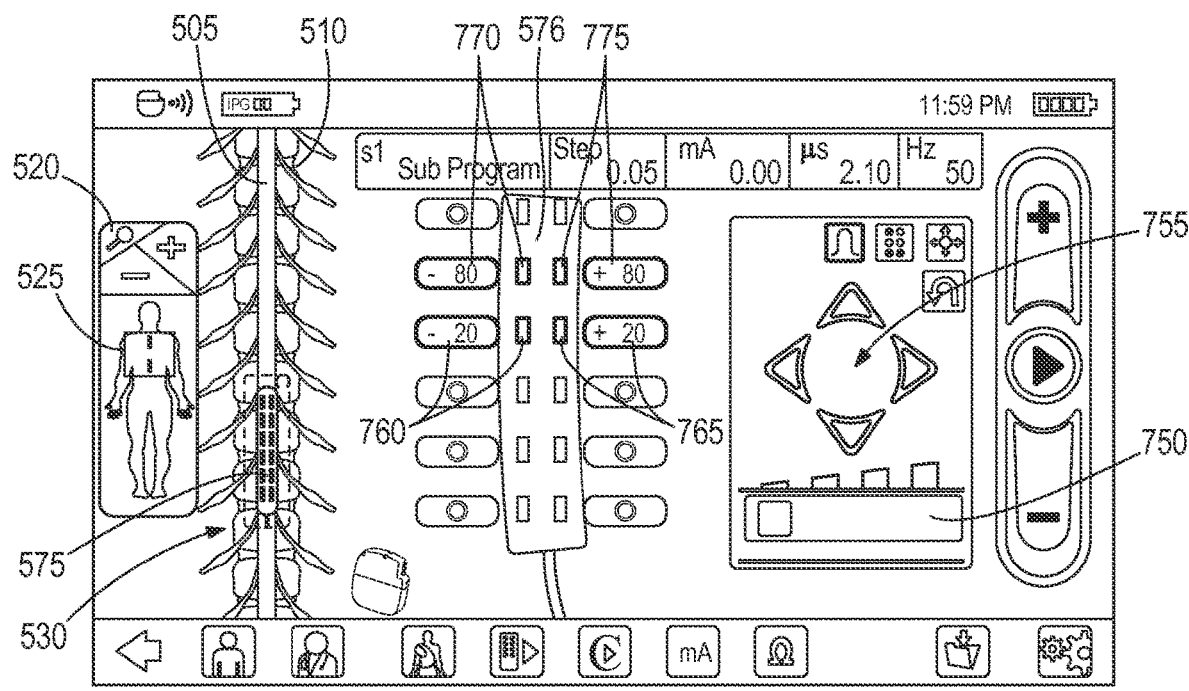

A fine parameter migration is shown in FIGS. 17-19. The fine parameter migration provides slower discretized parameter migration. In fine parameter migration, a granular lead configuration is discretely moved into the direction specified by the user (HCP). This provides slower discretized parameter migration as shown in FIGS. 17-19, which shows the user migrating the amplitude parameters in a downwards migration.

With specific reference to FIG. 17, a screen image is provided with an enlargement pane 520, a partial anatomical representation of a spinal column 505/510 with a lead 575 placed on the representation, and an exploded virtual representation of the electrode array 575 with electrode stimulation information associated with the array 575. The screen image also includes the first user-controllable input 750 configured for receiving a first input that defines an amount of amplitude change for a discrete stimulus migration, and the second user-controllable input 755 configured for receiving a second input defining a direction for the migration. In FIGS. 17-19, the first user-controllable input 750 is set to its minimum setting of 10%. Other percentages are possible and the number of choices can vary. Three different fine migration settings are shown in FIGS. 17-19.

So with reference to FIGS. 17-19, for example, amplitude configurations for the set of electrodes move down 10 percent in response to a down input. Specifically, electrodes 770 and 775 change from −100% and +100%, respectively, in FIG. 17 to −90% and +90%, respectively, in FIG. 18, while electrodes 760 and 765 change from 0%, in FIG. 17, to −10% and +10%, respectively, in FIG. 18. A second migration is shown between FIG. 18 to FIG. 19.

In one method of operation, each migration is triggered by an interrupted user input that provides a safe programming session for the patient. Multiple parameter migrations require multiple user inputs. The emphasis in this operation is on the capability that a discrete and interrupted system provides a safe and hazardless environment both for the HCP and the patient. The rate and amount of migration is discrete and completely under the control of the HCP. The HCP is given directional controls to migrate the electrode configuration. This overcomes shortcomings of prior methods were the HCP does not have the opportunity to provide interrupted stimulation parameters to the patient, or to examine the safety and validity of the chosen setting. Such a method might expose the patient to unsafe parameters that may cause harm. With continuous uninterrupted parameter migration the HCP does not have ample time to observe the behavior of the stimulation as well as understand the effects of the stimulation or feedback from the patient.

It is also envisioned that other parameters (amplitude, frequency, pulse width, etc.) that define a 'program' may be selected for electrode migration. In addition, a combination of the parameters may also be chosen when performing the migration.

Figure 20:
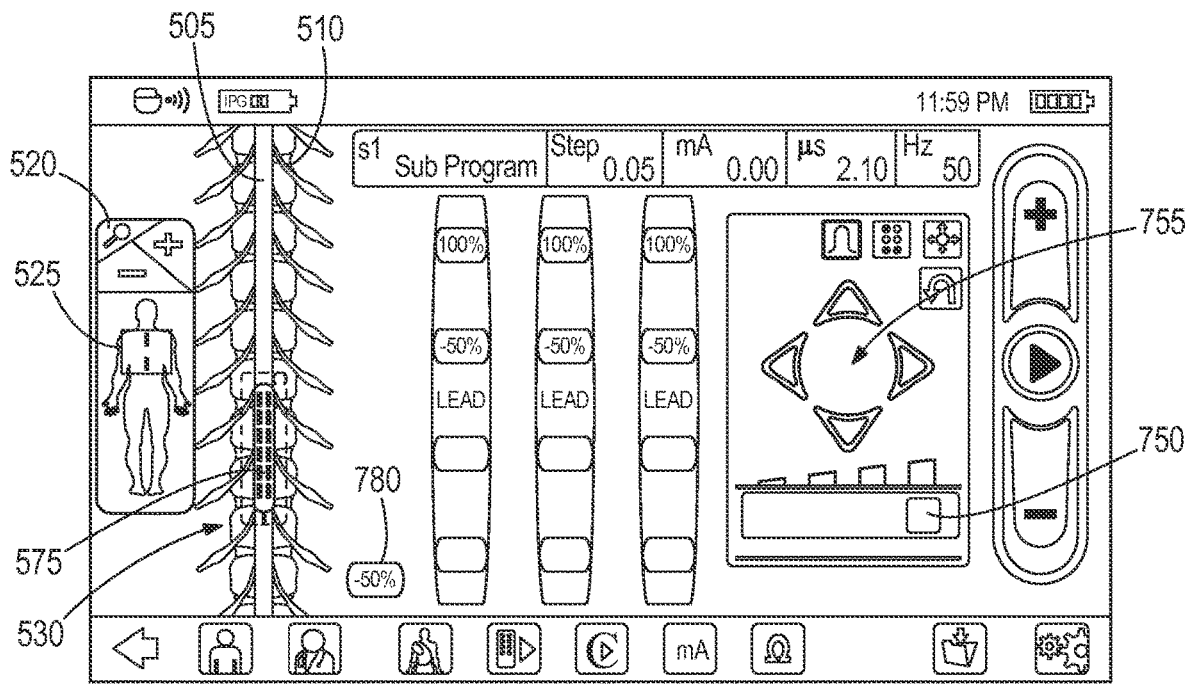
Figure 21:
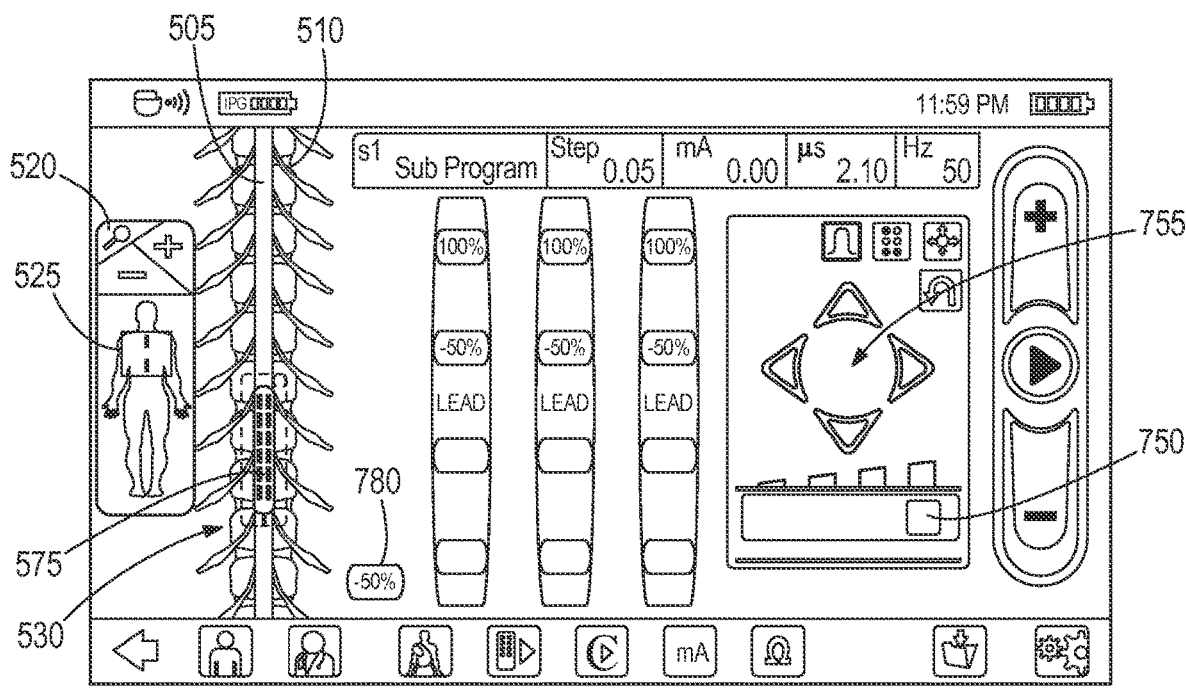

Furthermore, the CP 130 also provides a mechanism to selectively exclude electrodes from being considered for migration. An example of such a scenario is a program that uses the case or can as an electrode, as shown in FIGS. 20 and 21. In such a configuration, the can electrode 780 is not considered for parameter migration. FIGS. 20 and 21 show a coarse migration in the right direction with the can value of −50% is excluded from the migration.

Thus, the invention provides, among other things, useful and systems and methods for creating a program for electrical stimulation. Various features and advantages of the invention are set forth in the following claims.

What is claimed is:

1. A programmer for developing a program to provide therapeutic electrical stimulation to a patient with an electrical stimulation generator and an implanted medical lead coupled to the electrical stimulation generator, the implanted medical lead including a plurality of electrodes, the programmer comprising:
 a first user-controllable input configured for receiving a first input selecting an amount of amplitude change for a discrete stimulus migration;
 a second user-controllable input configured for receiving a second input selecting a direction for the migration, wherein the first user-controllable input and the second user-controllable input are displayed simultaneously via a graphical user interface of the programmer;
 a third user-controllable input configured for receiving a stimulation amplitude parameter, wherein the third user-controllable input is different from the first user-controllable input and the second user-controllable input;
 a processor configured for receiving the first input, receiving the second input, and calculating second stimulation parameters using first stimulation parameters, the first input, and the second input, the first stimulation parameters including assigned first amplitude values and first polarities for a first set of the plurality of electrodes and the second stimulation parameters including assigned second amplitude values and second polarities for a second set of the plurality of electrodes, the second amplitude values being different from the first amplitude values; and
 a transmitter configured for communicating the second stimulation parameters to the stimulation generator resulting in cessation of a first stimulation and initiation of a second stimulation with the stimulation generator using the second stimulation parameters.

2. The programmer of claim 1, further comprising:
 a housing supporting the processor and the transmitter; and
 a touch screen configured to display the graphical user interface.

3. The programmer of claim 2, wherein the graphical user interface is further configurable to display an anatomical representation of a spinal column and a representation of the lead placed with respect to the spinal column, wherein the representation of the lead includes representations of the plurality of electrodes selectable by a user.

4. The programmer of claim 1, wherein the second set of electrodes and the first set of electrodes are the same electrodes.

5. The programmer of claim 1, wherein the first user-controllable input is further configured for receiving indication to move an entire electrode configuration from a first electrode to a second electrode based on the second input defining the direction for the migration.

6. The programmer of claim 1, wherein the first user-controllable input is further configured for receiving indication to move a granular amount of electrode configuration from a first electrode towards a second electrode based on the second input defining the direction for the migration.

7. The programmer of claim 1, wherein the first user-controllable input includes a migration discretized amount selector.

8. The programmer of claim 1, wherein the first user-controllable input includes a directional input device.

9. The programmer of claim 1, wherein the processor is further configured for discretely revising stimulation parameters by repeatedly calculating second stimulation parameters using first stimulation parameter, the first input, and the second input.

10. The programmer of claim 1, wherein the implanted medical lead includes a plurality of medical leads.

11. The programmer of claim 1, wherein the amount of amplitude change is defined by a percentage.

12. An electronic programmer for programming a pulse generator to generate electrical stimulation to be delivered to a patient via an implantable lead coupled to the pulse generator, the electronic programmer comprising:
- a user interface configured to receive an input from a user and communicate an output to the user;
- a communications component configured to conduct electronic communications with external devices, the external devices including the pulse generator;
- a memory storage component configured to store programming code; and
- a computer processor configured to execute the programming code to perform operations that include:
  - simultaneously displaying, via the user interface, a first control mechanism and a second control mechanism that is separate and different from the first control mechanism;
  - displaying, via the user interface, a third control mechanism that is different from the first control mechanism and the second control mechanism;
  - receiving a first user input via the first control mechanism;
  - receiving a second user input via the second control mechanism;
  - receiving a third user input via the third control mechanism;
  - in response to the received third user input, setting a stimulation amplitude for the electrical stimulation; and
  - in response to the received first user input and the second user input, sending instructions to the pulse generator to cause a migration of the electrical stimulation from a first set of electrodes on the implantable lead to a second set of electrodes on the implantable lead, wherein the first user input selects a stimulation amplitude change for the migration, and wherein the second user input selects a direction for the migration.

13. The electronic programmer of claim 12, wherein:
the migration occurs in a plurality of steps; and
the first user input defines an automatic percentage change in amplitude in each of the plurality of steps.

14. The electronic programmer of claim 12, wherein the operations further comprise: displaying a virtual representation of the lead and a percentage of electrical stimulation assigned to the first set and the second set of electrodes throughout the migration.

15. The electronic programmer of claim 12, wherein the migration, once initiated, is performed automatically without requiring further manual user input.

16. The electronic programmer of claim 12, wherein the operations further comprise: excluding an electrode from the migration.

17. A medical system, comprising:
- a pulse generator configured to generate electrical stimulation for a patient;
- an implantable lead coupled to the pulse generator, the implantable lead having a plurality of electrodes, each of which is capable of delivering the electrical stimulation to the patient; and
- an electronic programmer that is configured to:
  - simultaneously provide a first control mechanism and a second control mechanism that is separate and different from the first control mechanism;
  - displaying a third control mechanism that is different from the first control mechanism and the second control mechanism;
  - receive a first user input via the first control mechanism;
  - receiving a second user input via the second control mechanism;
  - receiving a third user input via the third control mechanism;
  - in response to the received third user input, setting a stimulation amplitude for the electrical stimulation; and
  - in response to the received first user input and the second user input, communicate instructions to the pulse generator to cause a migration of the electrical stimulation from a first group of the plurality of electrodes to a second group of the plurality of electrodes, wherein the first user input selects a stimulation amplitude change for the migration, and wherein the second user input selects a direction for the migration.

18. The medical system of claim 17, wherein:
the migration occurs in a plurality of steps; and
the first user input defines an automatic percentage change in amplitude in each of the plurality of steps.

19. The medical system of claim 17, wherein the electronic programmer is further configured to: display a virtual representation of the lead and a percentage of electrical stimulation assigned to the first group and the second group of the plurality of electrodes throughout the migration.

20. The medical system of claim 17, wherein the migration, once initiated, is performed automatically without requiring further manual user input.

* * * * *